United States Patent [19]
Constantz

[11] Patent Number: 5,900,254
[45] Date of Patent: * May 4, 1999

[54] CARBONATED HYDROXYAPATITE COMPOSITIONS AND USES

[75] Inventor: Brent R. Constantz, Los Gatos, Calif.

[73] Assignee: Norian Corporation, Cuperino, Calif.

[*] Notice: This patent is subject to a terminal disclaimer.

[21] Appl. No.: 08/670,514

[22] Filed: Jun. 27, 1996

Related U.S. Application Data

[63] Continuation of application No. 07/963,481, Oct. 16, 1992, which is a continuation-in-part of application No. 07/918,233, Jul. 23, 1992, Pat. No. 5,336,264, which is a continuation-in-part of application No. 07/722,880, Jun. 28, 1991, abandoned, which is a continuation-in-part of application No. 07/650,462, Feb. 4, 1991, abandoned, which is a continuation-in-part of application No. 07/393,579, Aug. 14, 1989, Pat. No. 5,129,905, which is a continuation-in-part of application No. 07/358,716, May 30, 1989, Pat. No. 5,047,031, which is a continuation of application No. 07/183,770, Apr. 20, 1988, Pat. No. 4,880,610.

[51] Int. Cl.⁶ .......................... A61K 33/06; A61K 33/42; C01B 25/32; C01F 11/02

[52] U.S. Cl. .......................... 424/602; 424/601; 424/605; 424/606; 424/57; 423/305; 423/306; 423/307; 423/309; 606/76; 606/77; 623/16; 106/690; 106/691

[58] Field of Search .......................... 424/602, 57, 601, 424/605, 606; 423/300–301, 305–307, 309; 606/76, 77; 623/16; 106/690, 691

[56] References Cited

U.S. PATENT DOCUMENTS

| | | | |
|---|---|---|---|
| Re. 33,161 | 2/1990 | Brown et al. | 423/308 |
| Re. 33,221 | 5/1990 | Brown et al. | 427/440 |
| 3,647,371 | 3/1972 | Kim | 423/311 |
| 3,873,327 | 3/1975 | Duff | 106/35 |
| 3,913,229 | 10/1975 | Driskell | 433/228.1 |
| 4,048,300 | 9/1977 | Tomlinson et al. | 424/52 |
| 4,097,935 | 7/1978 | Jarcho | 623/16 |
| 4,139,599 | 2/1979 | Tomlinson | 423/308 |
| 4,170,658 | 10/1979 | Skinner | 423/430 |
| 4,279,661 | 7/1981 | Strauch | 106/464 |
| 4,321,042 | 3/1982 | Scheicher | 433/201.1 |
| 4,324,772 | 4/1982 | Conn et al. | 423/309 |
| 4,335,086 | 6/1982 | Spencer | 423/308 |
| 4,429,691 | 2/1984 | Niwa | 606/77 |
| 4,481,174 | 11/1984 | Iino | 423/702 |
| 4,518,430 | 5/1985 | Brown et al. | 106/35 |
| 4,612,053 | 9/1986 | Brown et al. | 706/35 |
| 4,917,702 | 4/1990 | Scheicher | 623/16 |
| 4,959,104 | 9/1990 | Iino | 106/691 |
| 5,092,888 | 3/1992 | Iwamoto et al. | 623/16 |
| 5,149,368 | 9/1992 | Liu | 424/602 |
| 5,152,836 | 10/1992 | Hirano | 106/690 |
| 5,180,426 | 1/1993 | Sumita | 106/35 |
| 5,262,166 | 11/1993 | Liu et al. | 424/423 |
| 5,320,844 | 6/1994 | Liu | 424/422 |
| 5,322,675 | 6/1994 | Hakamatsu | 423/311 |
| 5,336,264 | 8/1994 | Constantz et al. | 623/16 |
| 5,338,356 | 8/1994 | Hirano et al. | 106/690 |
| 5,525,148 | 6/1996 | Chow et al. | 106/35 |
| 5,536,575 | 7/1996 | Imura et al. | 428/403 |
| 5,569,490 | 10/1996 | Imura | 427/212 |
| 5,571,493 | 11/1996 | Fulmer et al. | 423/308 |
| 5,580,623 | 12/1996 | Fulmer et al. | 428/34.1 |
| 5,683,496 | 11/1997 | Ison et al. | 106/35 |
| 5,709,742 | 1/1998 | Fulmer et al. | 106/690 |
| 5,782,971 | 7/1998 | Constantz et al. | 106/690 |

FOREIGN PATENT DOCUMENTS

| | | |
|---|---|---|
| 518908 | 10/1981 | Australia . |
| 2143733 | 9/1995 | Canada . |
| A 0026090 | 4/1981 | European Pat. Off. . |
| 0543 765 A 1 | 10/1992 | European Pat. Off. . |
| 0625 490 B 1 | 5/1994 | European Pat. Off. . |
| 0 639 366 A1 | 2/1995 | European Pat. Off. . |
| A 2096886 | 3/1972 | France . |
| 2 693 716 | 7/1992 | France . |
| 53-111000 | 9/1978 | Japan . |
| 57-70216 | 4/1982 | Japan . |
| 58-89288 | 5/1983 | Japan . |
| 59-56676 | 3/1984 | Japan . |
| 59-192365 | 9/1984 | Japan . |
| 62-4637 | 1/1987 | Japan . |
| 62-193482 | 7/1987 | Japan . |
| 63/252913 | 10/1988 | Japan . |
| 1-74591 | 3/1989 | Japan . |
| 1-130-423 | 5/1989 | Japan . |

(List continued on next page.)

OTHER PUBLICATIONS

Chohayeb et al., "Evaluation of calcium phosphate as a root canal sealer–filler material," J. Endodontics (Aug. 1987) 13: 384–387.

Laurence Chow, "Development of Self–Setting Calcium Phosphate Cements," J. Ceramic Soc. Japan (1991) 99: 954–964.

Friedman et al, "Hydroxyapatite Cement," Arch Otol. Head Neck Surg. (Apr. 1991) 117: 385–390.

Fukase et al., "Setting reactions and compressive strengths of calcium phosphate cements," J. Dental Res. (Dec. 1990) 69: 1852–1856.

Mirtchi et al., "Calcium phosphate cements: study of the B–tricalcium phosphate–monocalcium phosphate system," Biomaterials (Sep. 1989) 10: 475.

Mirtchi et al., "Calcium phosphate cements: study of the B–tricalcium phosphate–dicalcium phosphate–calcite cements," Biomaterials (Mar. 1990) 11: 84.

(List continued on next page.)

Primary Examiner—John Pak
Attorney, Agent, or Firm—Townsend and Townsend and Crew, LLP; Bret Field

[57] ABSTRACT

Carbonated hydroxyapatite compositions and their preparation are described. The compositions are biologically resorbable and are prepared as flowable masses which can be administered by syringe to set in situ to serve as a support structure, filler, prosthesis or the like. Optionally the compositions may include proteins or serve as a depot for compositions of phrarmacological interest.

14 Claims, No Drawings

FOREIGN PATENT DOCUMENTS

| | | |
|---|---|---|
| 1-203801 | 8/1989 | Japan . |
| 1-266235 | 10/1989 | Japan . |
| 1-279811 | 10/1989 | Japan . |
| 1-310544 | 12/1989 | Japan . |
| 2-117444 | 5/1990 | Japan . |
| 2-117445 | 5/1990 | Japan . |
| 2-255082 | 9/1990 | Japan . |
| 3-123609 | 5/1991 | Japan . |
| 3-174349 | 7/1991 | Japan . |
| 3-283213 | 10/1991 | Japan . |
| 4-348754 | 12/1992 | Japan . |
| 4-348755 | 12/1992 | Japan . |
| 5-23386 | 2/1993 | Japan . |
| 5-9383 | 2/1993 | Japan . |
| 5-319891 | 12/1993 | Japan . |
| 6-45494 | 6/1994 | Japan . |
| A 1487181 | 9/1977 | United Kingdom . |
| 2248 232 | 1/1992 | United Kingdom . |
| 2 260 977 | 5/1993 | United Kingdom . |
| WO 88/09769 | 12/1988 | WIPO . |
| WO 90/00892 | 2/1990 | WIPO . |
| WO 95/08304 | 3/1995 | WIPO . |
| WO 95/08319 | 3/1995 | WIPO . |
| WO 96/29144 | 9/1996 | WIPO . |

OTHER PUBLICATIONS

Roy et al., "Hydroxyapatite formed from coral skeletal carbonate by hydrothermal exchange," Nature (Jan. 25, 1974) 247:220–222.

Yu et al, "Self–setting hydroxyapatite cement: a novel skeletal drug delivery system for antibiotics," J. Pharmacuetical Science (Jun. 1992) 81: 529–531.

Mirtchi et al., Biomaterial (1991) 12:505–510.

Monma et al, Yogyo Kyokai–Shi (1984) 92:157.

Sanin, N. et al., "Effects of Additives on Setting Reaction of Calcium Phosphate Cement", AADR, Abstract No. 666 (Jan. 15, 1992).

Chow, S., "Calcium Phosphate Materials: Reactor Response," *Adv. Dent. Res.* (Aug. 1988) vol. 2:181–184.

Constantz, et al., "Pilot Investigations of A Calcium Phosphate Cement In A Rabbit Femoral Canal Model and A Canine Humeral Plug Model," *17th Annual Meeting of the Society for Biomaterials* May 1–5 (1991).

Le Maitre, et al., "Calcium Phosphate Cements for Medical Use: State of the Art and Perspectives of Development," *Silicate Industries* (1987) vol. 9–10:141.

Monma et al., "Properties of Hydroxyapatite Prepared by Hydrolysis of Tricalcium Phosphate," *J. Chem. Tech. Biotech.* (1981) vol.31: 15–24.

Okazaki, et al., "Crystallinity, Solubility, and Dissolution Rate Behavior of Fluoridated $CO_3$ Apatites," *J. Biomedical Mat. Res.* (1982) vol.16:851–860.

Nordstrom and Karlsson, "Carbonate–doped Hydroxyapatite," J. of Materials Science: Materials in Medicine (1990), 182–184.

Okazaki et al., "Solubility Behavior of $CO_3$ Apatites in Relation to Crystallinity," Caries Research (1981), 15:477–483.

Doi et al., "Carbonate Apatites From Aqueous and Non-aqueous Media Studied by ESR, IR, and X–ray Diffraction: Effect of $NH_4+$ Ions on Crystallographic Parameters," J. Dent. Res. (Feb. 1982), 61:429–434.

Hassan et al., "Mineralogical Studies on Bone Apatite and Their Implications for Radiocarbon Dating," Radiocarbon (1977), 19:364–374.

Chickerur and Mahapatra "Preparation of Arsenate and Carbonate Hydroxylapatites," J. Inst. Chemists (India) (May 1974), XLVI:57–58.

Vignoles et al., "Influence of Preparation Conditions on the Composition of Type B Carbonated Hydroxyapatite and on the Localization of the Carbonate Ions," Calcified Tissue International (1988), 43:33–40.

Nelson et al., "Effect of Carbonate and Fluoride on the Dissolution Behavior of Synthetic Apatites," *Caries Res.* (1983), 17:200–211.

Webster's Third New International Dictionary of the English Language Unabridged, G. & C. Marriam Co., MA, 1963, p. 893.

ial composition. For instance, octacalcium phosphate
CARBONATED HYDROXYAPATITE COMPOSITIONS AND USES This application is a continuation of application Ser. No. 07/963,481 filed on Oct. 16, 1992; which application is a continuation in part of application Ser. No. 07/918,233 filed Jul. 23, 1992 and now issued as U.S. Pat. No. 5,336,264; which application is a continuation in part of application Ser. No. 07/722,880 filed Jun. 28, 1991 and now abandoned; which application is a continuation in part of application Ser. No. 07/650,462 filed Feb. 4, 1991 and now abandoned; which application is a continuation in part Ser. No. 07/393,579, filed on Aug. 14, 1989 and issued as U.S. Pat. No. 5,129,905; which application is a continuation in part of application Ser. No. 07/358,716 filed May 30, 1989 and now issued as U.S. Pat. No. 5,047,031; which application is a continuation of application Ser. No. 07/183,770 filed Apr. 20, 1988, now issued as U.S. Pat. No. 4,880,610; the disclosures of which are herein incorporated by reference.

INTRODUCTION

1. Technical Field

The field concerns the preparation of substantially pure compositions of carbonate-substituted forms of hydroxyapatite, and the biomedical use of such compositions.

2. Background

A number of calcium phosphate minerals, such as hydroxyapatite, fluorapatite, octacalcium phosphate, whitlockite, brushite and monetite may have application as biocompatible materials. The various crystalline forms of the calcium phosphate minerals can confer different physical properties that may be more or less desirable for a specific biomedical application. For instance, octacalcium phosphate and whitlockite are less resorbable than brushite or monetite (Brown and Chow, *Ann. Rev. of Materials Science* (1976) 6:213–236).

Of particular interest are the apatites. Apatite is a general term for a wide range of compounds represented by the general formula $M^{2+}_{10}(ZO_4^{3-})_6Y^-_2$, where M is a metal atom, particularly an alkali or alkaline earth atom, $ZO_4$ is an acid radical, where Z may be phosphorous, arsenic, vanadium, sulphur, silicon, or may be substituted in whole or in part by carbonate ($CO_3^{2-}$), and Y is an anion, usually halide, hydroxy, or carbonate. When $ZO_4^{3-}$ is partially or wholly replaced by trivalent anions (such as $CO_3^{2-}$) and/or $Y^-$ is partially or wholly replaced by divalent anions, then charge balance may be maintained in the overall structure by additional monovalent cations (such as $Na^+$) and/or protonated acid radicals (such as $HPO_4^{2-}$).

Hydroxyapatite (HAp), as well as its various forms, has been the focus of substantial interest because it is a major structural component of biological tissues such as bone, teeth, and some invertebrate skeletons. There are many situations where bone has been broken, surgically removed, destroyed, degraded, become too brittle, or been subject to other deteriorating effects. In many of these situations it would be desirable to be able to replace the bone structure or strengthen the bone structure. In providing materials to substitute for natural bone, teeth, or other calcified tissues, there are a number of restraints on the natural composition of the material.

Dental applications might prefer a fluoride substituted hydroxyapatite, i.e. francolite, that would reduce solubility and increase resistance to decay.

The material should ideally possess certain characteristics that facilitate the production, storage life, and biomedical application of the material. Specifically, a material which could be a material which could be fingerpacked in an open surgical procedure or percutaneously injected as a flowable composition to fill voids or completely fill-in areas deficient of hard bone is very desirable. Where the material is to be placed in the body and formed and hardened in situ, a variety of considerations come to the fore. For example, the rate at which hydroxyapatite forms as well as the extent to which the formation of hydroxyapatite is exothermic or may generate gas can also be important. Where the reaction is highly exothermic, it may cause thermal necrosis of the surrounding tissue.

As the final form of the material must be stable under physiological conditions, so must the form in which the material is introduced be stable while it is hardening in the environment to which it is introduced, as must be any intermediate products of the formation reaction.

The material should also be physiologically acceptable at all phases of curing to the final product, so as to avoid the initiation of clotting, inflammatory responses, and the like. Two different forms of apatite are particularly desirable: One being an hydroxyapatite or a fluoridated derivative thereof that is non-resorbable in vivo; the other includes forms of apatite that are substantially resorbable in vivo. In addition, both forms of apatite must usually be strong and non-friable. Furthermore, there should be a strong adhesion between the material and the remaining bone or calcified tissue. Also, the material should desirably be able to substitute some of the other functions of natural bone such as: accommodating stem cells; allowing infiltration by cells normally resident in natural bone such as osteoclasts, osteoblasts, and the like; allowing remodeling of the material by the infiltrating cells followed by new bone in-growth; and acting in metabolic calcium exchange in a manner similar to native bone.

Carbonate has been shown to inhibit crystal growth of HAp (Blumenthal, et al., *Calcif. Tissue Int.* (1984) 36:439–441; LeGeros, et al., "Phosphate Minerals in human tissues", in *Phosphate Minerals* (Berlin), J. Nriagu (eds): Springer, 1984, pp. 351–385; LeGeros, et al., *J. Dent. Res.* (1989) 68:1003; Nauman and Neuman, The Chemical Dynamics of Bone Mineral, University of Chicago Press, Chicago, (1958); Newesley, *Arch. Oral Biol.* (1961) 6:174–180; Posner, *Clin. Orthop.* (1985) 200:87–99). Carbonates are present in the apatites of hard tissues, and their presence alters the properties of stoichiometric apatite. Carbonate has been described as causing: 1) a reduction in crystallite size, 2) changes in the morphologies of the mineral phase from needles and rods to equi-axis crystals (spheroids), 3) contraction of the a-axis, as well as an expansion in the c-axis, 4) internal strain, and 5) chemical instability (LeGeros, et al., supra, 1984; LeGeros, et al., supra, 1989). All of these factors lead to higher solubilities of carbonate-substituted HAp. The x-ray diffraction patterns as well as the radial distribution function are changed considerably in that as the concentration of carbonate increases, the patterns become more amorphous in character (LeGeros et al., supra 1989; Glimcher, M. J., "Recent studies of the mineral phase in bone and its possible linkage to the organic matrix by protein-bound phosphate bonds", *Phil. Trans. R. Soc. London Ser.* B., 304, 479–508). The line broadening observed in the diffraction pattern is caused by decreasing crystallite size and crystallinity. In addition to inhibiting HAp crystal growth, carbonate substitution markedly increases the solubility of HAp (Nelson, et al., *Ultramicroscopy* (1986) 19:253–266. Another interesting experimental finding was that, whether the carbonates are structurally bound within, or absorbed onto HAp, differences in dissolution behavior were observed. This suggests that dissolution increased in HAps containing structurally bound carbonates, while decreasing in HAps with absorbed $CO_3^{2-}$. The decrease in dissolution was explained by the fact that hydronium ions had to compete for the surface of HAp, hence the deposition of the $CO_3^{2-}$ layer was required.

The extent of carbonate uptake during HAp precipitation under normal physiologic conditions is approximately 1% by weight $CO_3^{2-}$ (Posner, supra, 1985). Bone consists of approximately 4% by weight $CO_3^{2-}$. Thus, HAp precipitation reactions in air generally contain relatively low concentrations of carbonate. Bone mineral apatite with a level of carbonate between 2% and 10% by weight has been referred to by convention as dahllite (McConnell, *J. Dent. Res.* (1952) 31:53–63 and McConnell, *Clin. Orthonaed.* (1962) 23:253–268).

Carbonates can substitute in both the Z and Y sites of the apatite structure, and it is generally accepted that carbonates substitute for $PO_4^{3-}$ groups during precipitation reactions leading to HAp formation. More specifically, HAp products formed at lower temperature exhibit carbonate substitution at the phosphate sites, and due to its smaller size, a decrease in the a-axis of the apatite results (LeGeros, et al., supra, 1984 and LeGeros, et al., supra, 1989). Conversely, in most high temperature apatites, the carbonates are found in the vicinity of the six fold axis, where they replace hydroxyl ions. Since the carbonate is larger than the hydroxl ion, an increase in the a-axis results (Brown and Chow, (1986), supra).

The skeleton is the reservoir for almost all of the body's calcium and most of its phosphorus and magnesium (Avioli and Krane, *Metabolic Bone Disease and Clinically Related Disorders*, 2nd Ed., 1990, W. B. Saunders Co., Philadelphia, p. 2). The carbonate levels in human enamel have been shown to increase in concentration from the surface to the dentin. The carbonate concentration in the surface enamel has also been shown to decrease with age (Brudevold and Soremark, Chemistry of the mineral phase of enamel, Miles (ed.), In: *Structural and Chemical Organizations of Teeth*. Academic Press, New York, 1967, Vol. II, p. 247. The ease of ionic substitution in the lattice of apatite allows for the ionic substitution of ions from the fluids surrounding the bone, and vice versa. This implies that hard tissues act as a regulatory reservoir for certain ions by incorporating ions into its structure when ionic concentration in the serum rises too high, and dissolving ions when the body is deficient in them. Possible candidates for this form of regulation might include some of the inorganic constituents of serum such as ionized and complexed calcium, inorganic phosphates, magnesium, bicarbonate, sodium, chloride, potassium, among others (Eidleman, et al., *Calcif. Tissue Int.* (1987a) 41:18–26; Eidelman, et al., *Calcif. Tissue Int.* (1987b) 40:71–78; Meyer and Fleisch, *Miner. Electrolyte Metab.* (1984) 10:249–258).

Carbonate is especially important in hard tissue in that it apears to be required for the cellular infiltration of bone by osteoclasts, osteoblasts and other bone resident cells. Since osteoclasts, osteoblasts and the like are involved in mineral replacement and bone remodeling, any synthetic apatite-associated bioimplant would preferably use a carbonated form of apatite, or dahllite. Because dahllite can be remodeled by the bodies natural processes, the dahllite component of an implant should, through the action of osteoclasts and osteoblasts, eventually be replaced by natural bone. Thus, dahllite implants should eventually gain many or all of the desirable features of natural bone such as increased strength, elasticity and durability.

Previous methods of chemically forming monolithic bodies of hydroxyapatite have not produced dahllite or hydroxyapatites with physiologically significant levels of structurally incorporated carbonate. This is primarily because the acid present in the reactions of other methods tend to react with the carbonate to produce gaseous $CO_2$. Gaseous escape removes carbonate from the reaction which is forming apatite and can result in a product that is substantially more friable than that generally desired by virtue of the trapped gas bubbles disrupting the structural integrity of the product. Thus, a major obstacle to the production of dahllite has been devising a method to maintain carbonate in the product despite the presence of the acid required to form the apatitic structure.

Relevant Literature

Patents of interest include U.S. Pat. Nos. 3,787,900; 3,913,229; 3,679,360; 4,097,935; 4,481,175; 4,503,157; 4,612,053; 4,659,617; and 4,693,986. See also, Arends and Jongebloed, *Rec. Trav. Chim. Pays-Bas* (1981) 100:3–9. Use of calcium phosphate as a sealer-filler material is described in Chohayeb et al., *J. Endodontics* (1987) 13:384–387 and Lowenstam and Weiner, *On Biomineralization*, (1989), Oxford University Press, New York. See also, Ohwaki et al., 13th Ann. Mtg. of the Soc. for Biomaterials, Jun. 2–6, 1987, New York, N.Y., p209.

SUMMARY OF THE INVENTION

Compositions comprised of dahllite, analogs thereof, or otherwise carbonate-substituted forms of hydroxyapatite (dahllite-like compositions) are provided that are useful in a variety of biomedical applications. The compositions can be prepared such that they are flowable, moldable, and capable of hardening in situ. The compositions harden into monolithic polycrystalline structures that can be shaped subsequent to hardening.

DESCRIPTION OF THE SPECIFIC EMBODIMENTS

Compositions are provided that are comprised of substantially pure (greater than 80% by weight) dahllite-like compositions referred to as carbonated hydroxyapatite that can be produced substantially free of the blood-borne or organic components of natural bone. The compositions can be used to substitute many of the functions of naturally occurring calcified tissues or in the repair of such tissues, in particular teeth and bone. The dahllite or francolite-like products can be readily formed by combining the wet and dry reactants to provide a substantially uniform mixture, shaping the mixture as appropriate, and allowing the mixture to harden. During hardening, the mixture crystallizes into a solid and essentially monolithic apatitic structure. The dahllite and francolite-like apatitic compositions can also be shaped subsequent to hardening. Alternatively, the dahllite or francolite-like apatitic compositions can be precursor reaction mixtures placed into an appropriate section of the body and hardened and/or shaped in situ.

The composition of the carbonated hydroxyapatite may vary, frequently being non-stoichiometric in having incorporated extra hydrogen atoms. Also, the calcium/phosphate ratio may vary, where the ratio may be as low as 1.33 (1.67 is the natural ratio), so that there is a defective lattice structure from the calcium vacancies and as high as 2.0. For a ratio of 1.33, there will be two calcium ions absent. The extra hydrogens may be up to about 2 hydrogen ions per phosphate, usually not more than about one hydrogen ion per phosphate. The ions will be uniformly distributed throughout the product and for the most part, the composition will be monophasic having a single crystal structure. As compared to sintered hydroxyapatite and hydrothermally prepared hydroxyapatite, the X-ray diffraction and Fourier transform infra-red spectra of the subject compositions are substantially different.

The reactants will generally consist of a phosphoric acid source substantially free of unbound water, an alkali earth metal, particularly calcium, source, optionally crystalline nuclei, particularly hydroxyapatite or calcium phosphate crystals, calcium carbonate, and a physiologically acceptable lubricant, such as water, which may have various solutes. The dry ingredients may be pre-prepared as a mixture and subsequently combined with the liquid ingredients under conditions where substantially uniform mixing occurs. Where gases are evolved the mixture is agitated to cause the release of large pockets of gas.

The phosphoric acid source may be any partially neutralized phosphoric acid, particularly up to and including complete neutralization of the first proton as in calcium phosphate monobasic. Alternatively or additionally, it can consist of orthophosphoric acid, possibly in a crystalline form, that is substantially free of combined water. The acid source will generally be about 15 to 35 weight percent of the dry components of the mixture, more usually 15 to 25 weight percent.

In selecting the calcium source, particularly where the calcium source serves a dual role of providing calcium and acts in a neutralizing capacity, one must consider that the desired final product will depend on the relative ratios of calcium and phosphate. Calcium sources will generally include counterions such as carbonate, phosphate or the like. Of particular interest are dual sources of calcium phosphate and phosphate such as tetracalcium phosphate ($C_4P$) or tricalcium phosphate ($C_3P$). Tetracalcium phosphate or tricalcium phosphate may typically be present in the mixture at from about 0 to 70 weight percent, more usually from about 0 to 40 weight percent, and preferably from about 2 to 18 weight percent of dry weight of the dry components of the mixture. With calcium carbonate present to neutralize the acid and to serve as a source of calcium and carbonate, the reaction will result in relatively little temperature rise; however, there is substantial evolution of gas which must be released during mixing. Calcium carbonate will be present in the mixture from about 2 to 70 weight percent, more usually from about 2 to 40 weight percent, and preferably from about 2 to 18 weight percent of dry weight of the dry components of the mixture Calcium hydroxide may also be present in the mixture from about 0 to 40 wt. %., more usually from about 2 to 25 wt. %, and optimally from about 2 to 20 wt. %.

Halides such as fluorine and chlorine may be added to form fluorapatite (francolite), or chlorapatite respectively. Various sources of fluoride or chloride may be employed. Generally, the sources will include either soluble salts such as calcium chloride, calcium hexafluorosilicate or sodium fluoride or, less desirably, the source may be added as a dilute acid in the aqueous lubricant, generally at concentrations of less then about 1M. Halides, if present at all, will constitute from about 0 to 4 weight percent, more usually from about 2 to 4 weight percent, preferably from about 3 to 4 weight percent of dry weight. Usually at least about 5, more usually at least about 10% of the hydroxyl groups will be replaced, and up to 100%. Francolite is of particular interest because of the potential dental applications of this partially fluorine substituted form of dahllite.

The various dry components may be combined prior to the addition of the wet components. Mixing will be used to combine the ingredients and can be used to regulate the extent of the inter-ingredient reactions. Any or all of the dry ingredients may be added prior to the initiation of mixing or prior to the completion of mechanical mixing. Methods of mixing can include ball milling, Brabender mixing, rolling between one or more rollers and a flexible container, or the like. Preferably, mixing will be thorough and will occur for a relatively short time or until a uniform dispersal of ingredients is obtained.

By varying the proportion of liquid lubricant, particularly water, added to the subject mixtures, the fluidity of the composition can be varied with respect to flowability and viscosity. Besides or in combination with water, other water miscible pharmacologically acceptable liquids may be used, particularly alkanols, more particularly polyols, such as ethylene glycol, propylene glycol or glycerol, usually being present in less than about 10 volume percent in an appropriate medium. The liquid will generally be from about 15 to 50, more usually from about 20 to 35 weight percent of the entire composition. Various solutes may be included in the aqueous medium. Of particular interest is the use of a gel or colloid, which has as a solute alkali metal hydroxide, acetate, phosphate, or carbonate, particularly sodium, more particularly phosphate or carbonate, at a concentration in the range of 0.01 to 2 m, particularly 0.05 to 0.5 m, and at a pH in the range of about 6–11, more usually about 7–9, particularly 7–7.5.

Implantation may be by syringe or catheter injection; particularly, the composition may be used as a paste that passes through a needle in the range of about 10–18 gauge, preferably about 14–16 gauge. Alternatively, if less lubricant is added, the composition is kneadable or moldable, being capable of forming clay-like putty that may be molded prior to setting. By varying the amount of lubricant employed, the setting time of the compositions can also be varied.

After mixing, the mixture is allowed to anneal while remaining quiescent, followed by an extended period of time during which the mixture hardens. During hardening, crystal growth occurs and the product becomes an integral mass. Hardening will take at least about 5 minutes, usually at least about 15 minutes, and not more than about 20 minutes. Compounds produced in this manner will have a wide variety of desirable properties for use in physiological applications.

The claimed compositions will contain, structurally incorporated into the apatitic structure, between about 2% and about 10% carbonate by weight, usually between 2.5% to 7%, and optimally between about 4% to about 6% carbonate by weight.

The subject compositions are biocompatible having a pH in the range of about 5.5–8.5, usually in the range of about 6–7.5. They can be prepared so that they can be administered to an environment having a temperature in the range of about 0–45° C., usually 20–40° C., and optimally about normal physiological temperature, 37° C. The compositions have low or no toxicity when prepared in accordance with described methods, are substantially inactive as to detrimental interactions with various host components in vivo, and are readily implantible. Furthermore, they are readily resorbable in vivo so as to be replaced by natural bone.

Various additional components may be included during the formation of the carbonated hydroxyapatite, dahllite. Of particular interest are pharmacologically active agents, proteins, polysaccharides, or other biocompatible polymers, or the like. Of particular interest are proteins involved in skeletal structure such as different forms of collagen, especially Type I, fibrin, fibrinogen, keratin, tubulin, elastin, and the like, or structural polysaccharides, such as chitin. Pharmacologically active agents might include drugs that enhance bone growth, serve as a variety of cell growth factors, or act as anti-inflammatory or anti-microbial agents. Examples of such proteins might include but not be limited to: bone morphogenetic protein, cartilage induction factor, platelet derived growth factor, and skeletal growth factor. Pharmacologically active or structural proteins may be added as an aqueous dispersion or solution. Usually the protein will be present in from about 1–10 wt % of the aqueous dispersion. The protein will be present in the final composition after setting in from about 0.01 to 10, usually from about 0.05 to 5 weight percent. The amount of water added to the compositions to which protein in aqueous dispersion has also been added will be adjusted accordingly. By varying the proportions of the reactants, compositions with varying and predictable rates of resorption in vivo, can be made. Thus, the subject compositions enable one of ordinary skill in the art to add drug and inorganic components both subsequent to and during, and possibly prior to, the formation of the subject compositions in order to practice an implantible or injectable time-release delivery platform for drugs, inorganic mineral supplements, or the like.

When used as cements or fillers, the subject compositions bond to other apatites when applied to an apatitic surface, such as bones or teeth which are mainly comprised of dahllite and collagen. The applicable compositions are able to strongly adhere and bond to surfaces that are wet or coated with saliva, blood or lymphatic fluid, will fill voids, and conform to irregular surfaces such as concavities and convexities. The compositions may be applied as a continuous mass without the formation of fragments or loose particles to a significant degree. Furthermore, the subject compositions are found to be structurally compatible in providing for the structural functions of replaced connective tissue.

The subject compositions can be used to form carbonated hydroxyapatite coatings on bioimplants or other formed objects.

The subject composition, as a flowable or formable product, can serve as a bone cement, or an infiltrate cement for the treatment of osteoporotic bone.

Paste or clay-lika mixtures of product are provided that may be formed and hardened into a monolithic carbonated hydroxyapatite product, either externally or in situ.

Of particular interest is preparation of the subject carbonated hydroxyapatite by a process whereby a calcium source, at least one component of which is calcium carbonate, and an acidic phosphate source, optionally comprised of ortho phosphoric acid crystals substantially free of uncombined water, are mechanically mixed for sufficient time for a partial reaction of said calcium source and acidic phosphate source. The partially reacted composition can be subsequently mixed with a physiologically suitable lubricant which varies the fluidity of the product, allows the substantially complete reaction of the reactants, and eventually results in a monolithic solid carbonated hydroxyapatite product. The final mixture may be subsequently shaped and hardened, hardened then shaped, or placed in the body and hardened in situ. The carbonated hydroxyapatite of the subject process will have substantially reduced or non-exothermic setting which may better provide for the stability of introduced pharmacological agents, and, when hardened in situ, is desirable for purposes of patient comfort. The compositions of this process are also applicable as bone cements or fillers, dental or endodontic filling agents, coatings for bioimplantible substrates, or formed into suitable shapes before or after hardening into a monolithic structure.

The calcium source used in the above process will typically include a mixture of tetracalcium phosphate ($C_4P$) and calcium carbonate (CC) with $C_4P$ typically present in from about 55 to 75 wt. %, or more usually 60–70 wt. %, and CC typically present in from about 1 to 40 wt. %, or more typically 2 to 18 wt. % of the dry weight of the total reaction mixture.

The acid phosphate source will be about 15 to 35, or more usually 15 to 25 wt. % of the dry weight of the reaction mixture.

An alternative formula will typically include a mixture of tricalcium phosphate ($C_3P$), calcium carbonate (CC), and calcium hydroxide (CH) with $C_3P$ typically present in from about 50 to 90 wt. %, or more usually 75 to 90 wt. %, CC typically present from about 1 to 40 wt. % or more usually 2 to 18 wt. %, and CH typically present from about 0 to 40 wt. % or more usually 2 to 20 wt. % of the dry weight of the total reaction mixture.

The acid phosphate source for this alternative mixture will be about 5 to 35 wt. % or more usually 5 to 25 wt. % of the dry weight of the reaction mixture.

A fluoride source may generally be added to the mixture and, if at all present, will be in an amount from about 0 to 4 wt. %, preferably 3 to 4 wt. % of dry weight.

After the dry ingredients are combined, the reactants will be placed in intimate contact by mechanical mixing or milling. Prior to the completion of mixing/milling, proteins and/or small organic molecules, especially those containing pharmacological significance as indicated earlier, may be added to the mixture to alter the physical or physiological properties of the final product. The amount of additive will generally vary from about 1 to 40 weight percent, more usually from about 1 to 25 weight percent of the inorganic materials. It may be preferred that the additive be combined with the inorganic materials before mixing/milling.

Mechanical mixing may be by any form that results in an intimate mixing of the reactants. A variety of equipment may be used for these purposes including ball mills, planetary mills, centrifugal mills, mechanofusion systems, air pulverizers, jet mills, vibratory mills, colloid mills, attrition mills, disc mills, and the like.

The course of mixing can be monitored by periodically removing samples and testing whether or not the samples result in the formation of a product with the desired properties after mixing with as aqueous medium and subsequent hardening.

During mixing or milling, the walls of the mixing vessel may be periodically scraped to better promote a more uniform product. The milling media should remain stable as inert throughout the process as would media such as alumina, zirconia, tungsten carbide, boron carbide, etc.

The product of the above process will have undergone a relatively stable partial reaction and will require less lubricant to provide a workable mixture as well as a reduced setting time.

All of the above-mentioned products or their precursors may be sterilized by gamma-irradiation or other applicable methodologies prior to bioimplantation.

The following example is offered by way of illustration and not by way of limitation.

EXPERIMENTAL

Example 1

In a chilled mortar, 11.54 g of tetracalcium phosphate (TCP), 1.40 g of calcium carbonate, 2.06 g of orthophosphoric acid and 7.5 g of 0.01 m sodium phosphate were mixed with a chilled pestle (mixed bases for 15 sec., followed by 30 sec. of mixing of both acid and bases, then 3 min. of wet mixing of the combined solution, acids and bases). The completed mixes were injectable and free flowing and were immediately put into bovine serum with (0.1% sodium azide) and cured at 37° C. for about 2 weeks. At the end of the 2 week cure, the samples were rinsed with deionized water, frozen in liquid nitrogen, then lyophilized overnight. Sample aliquots were analyzed by Fourier transform infrared spectroscopic analysis (FTIR) using pressed KBr pellets and by carbon coulometry using acidification for total inorganic carbon analysis and by combustion for total carbon analysis. The samples were further assayed for carbonate content in duplicate. The results of these assays are presented in Table 1 which shows that the subject compositions reacted to form carbonated hydroxyapatite having a dahllite crystal structure as confirmed by the weight percentage of carbonate contained in the resulting apatites.

TABLE 1

| | Formulation | Mineralogy | % Carbonate |
| --- | --- | --- | --- |
| A | 11.54 g C$_4$P(c), 1.4 g CC, 2.06 g oPA, 7.5 g 0.1M SP | 98% Dahllite | 4.53 |
| B | 11.54 g C$_4$P(f), 1.4 g CC, 2.06 g oPA, 7.5 g 0.1M SP | 98% Dahllite | 4.83 |

Abbreviations:
C$_4$P = Tetracalcium phosphate, fine (f) 3 microns, course (c) 10 microns.
CC = Calcium carbonate.
oPA = Ortho-phosphoric acid.
SP = Sodium phosphate, dibasic, 7-hydrate.

Example 2

A number of dry formulations were prepared having the compositions as set forth in Table 2.

TABLE 2

| Ingredient | 1 | 2 | 3 |
| --- | --- | --- | --- |
| Tetracalcium phosphate | 45.0 | 43.95 | 13.73 |
| Calcium oxides | 0.17 | 0.33 | 0.56 |
| Calcium carbonate | 5.85 | 11.4 | 4.0 |
| Ca(H$_2$PO$_4$)$_2$.H$_2$O | 15.5 | | |
| Orthophosphoric acid | | 11.76 | 4.41 |
| Na$_2$SiF$_6$ | 0.29 | 0.25 | 0.09 |

Each of the above formulations were ball milled in an alumina/silica mill jar with 0.5"×0.5" alumina cylinders, where the container was from 25 to 50 volume percent full. The milling usually was continued for about 16 hours. In many cases, some caking was observed, particularly at the top of the container. The gasket at the top of the container to enclose the cover was cut, so as to allow for the release of gas. The mixing was at about 50 rpm.

After completion of the milling, the composition was combined with water, generally using about 0.35 parts of water to 1 part of solids. For preparing samples, 5 g of the solid mixture was combined with 1.75 g of deionized water and the mixture kneaded for about 5 min. The composition was introduced into a mold, allowed to set, and the sample removed for compressive strength testing. In some instances, the samples could not be easily removed from the mold, which could have affected the observed compression properties. The following table indicates the results, where the results are reported as the average of from 3 to 4 determinations on different samples from the same composition.

TABLE 3

| Ex. | Weight (g) | Load (lbs.) | Compressive Strength (psi) |
| --- | --- | --- | --- |
| 1 | 0.72 | 367.9 | 8389 |

Considerable variation was noticed in the results. In example 1, the variation was from 5620 to 11794. Thus, while samples can be obtained having compressive strengths in substantial excess of 10,000 psi, the reasons why other samples from the same composition do not provide the same properties is believed to be related to defects in the specimen related to sample preparation. However, in any sample, products having properties in substantial excess of 10,000 psi compressive strength are achievable.

It is evident from the above results that the subject composition and the products derived therefrom provide a unique alternative to standard hydroxyapatite materials. Unlike standard hydroxyapatite compositions, the subject dahllite compositions can be constructed to contain carbonate at levels near or exceeding those normally occurring in natural bone. Since carbonate is intimately involved in the processes by which normal bone-resident cells are able to infiltrate, resorb and replace natural bone, the subject compositions provide products that better mimic natural calcified tissues in both form and function.

All publications and patent applications mentioned in this specification are indicative of the level of skill in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. A two-part calcium phosphate cement formulation that, when mixed, is capable of hardening and forming an integral mass, wherein said integral mass is substantially pure 2 to 10 wt % carbonate-substituted hydroxyapatite that (i) has a calcium/phosphate molar ratio of about 1,33 to 2.0, (ii) is not sintered or hydrothermally prepared, (iii) has a compressive strength ranging from about 5620 to 11794 psi, and (iv) is biocompatible, and which two-part calcium phosphate cement formulation contains:

as the first part dry ingredients comprising a partially neutralized phosphoric acid, a calcium phosphate source, and calcium carbonate in an amount ranging front about 9.33 to 70 wt % of said dry ingredients; and as the second part a physiologically acceptable aqueous lubricant solution selected from the group consisting of 0.01 to 2M sodium phosphate solution at pH 6 to 11 and 0.01 to 2M sodium carbonate solution at pH 6 to 11, wherein said aqueous lubricant solution is present in an amount ranging from about 15 to 50 wt % of the two-part calcium phosphate cement formulation.

2. The cement according to claim 1, wherein said partially neutralized phosphoric acid source is $Ca(H_2PO_4)_2.H_2O$.

3. The cement according to claim 1, wherein said calcium phosphate source is tricalcium phosphate.

4. A two-part calcium phosphate cement formulation that, when mixed, is capable of hardening and forming an integral mass, wherein said integral mass is substantially pure 2 to 10 wt % carbonate-substituted hydroxyapatite that (i) has a calcium/phosphate molar ratio of about 1.33 to 2.0, (ii) is not sintered or hydrothermally prepared, (iii) has a compressive strength ranging from about 5620 to 11794 psi, and (iv) is biocompatible, and which two-part calcium phosphate cement formulation contains:

as the first part dry ingredients comprising a partially neutralized phosphoric acid, a tricalcium phosphate, and calcium carbonate in an amount ranging from about 9.33 to 40 wt % of said dry ingredients; and as the second part a physiologically acceptable aqueous lubricant solution selected from the group consisting of 0.01 to 2M sodium phosphate solution at pH 6 to 11 and 0.01 to 2M sodium carbonate solution at pH 6 to 11, wherein said aqueous lubricant solution is present in an amount ranging from about 15 to 50 wt % of the two-part calcium phosphate cement formulation.

5. The cement according to claim 4, wherein said aqueous lubricant solution is a 0.01 to 2M sodium phosphate solution at pH 6 to 11.

6. The cement according to claim 4, wherein said partially neutralized phosphoric acid is $Ca(H_2PO_4)_2.H_2O$.

7. A two-part calcium phosphate cement formulation that, when mixed, is capable of hardening and forming an integral mass, wherein said integral mass is substantially pure 2 to 10 wt % carbonate-substituted hydroxyapatite that (i) has a calcium/phosphate molar ratio of about 1.33 to 2.0, (ii) is not sintered or hydrothermally prepared, (iii) has a compressive strength ranging from about 5620 to 11794 psi, and (iv) and is biocompatible, and which two-part calcium phosphate cement formulation contains:

as the first part dry ingredients comprising $Ca(H_2PO_4)_2.H_2O$, a tricalcium phosphate, and calcium carbonate in an amount ranging from about 9.33 to 18 wt % of said dry ingredients; and as the second part a 0.01 to 2M sodium phosphate solution at pH 6 to 11 present in an amount ranging from about 15 to 50 wt % of the two-part calcium phosphate cement formulation.

8. A kit for use in the preparation of a composition capable of hardening and forming air integral mass, wherein said integral mass is substantially pure 2 to 10 wt % carbonate-substituted hydroxyapatite that (i) has a calcium/phosphate molar ratio of about 1.33 to 2.0, (ii) is not sintered or hydrothermally prepared, (iii) has a compressive strength ranging from about 5620 to 11794 psi, and (iv) is biocompatible, said kit comprising:

dry ingredients comprising a partially neutralized phosphoric acid, a calcium phosphate source, and calcium carbonate in an amount ranging from about 9.33 to 70 wt % of said dry ingredients; and a physiologically acceptable aqueous lubricant solution selected from the group consisting of 0.01 to 2M sodium phosphate solution at pH 6 to 11 and 0.01 to 2M sodium carbonate solution at pH 6 to 11, wherein said aqueous lubricant solution is physically separated from the dry ingredients of said kit and is present in an amount ranging from about 15 to 50 wt % of the total weight of said dry ingredients and said aqueous lubricant of said kit.

9. The kit according to claim 8, wherein said partially neutralized phosphoric acid is $Ca(H_2PO_4)_2.H_2O$.

10. The kit according to claim 9, wherein said calcium phosphate source is tricalcium phosphate.

11. The kit according to claim 8, wherein said aqueous lubricant solution is a 0.01 to 2M sodium phosphate solution at pH 6 to 11.

12. The kit according to claim 8, wherein at least two of said dry ingredients are combined.

13. A kit for use in the preparation of a composition capable of hardening and forming an integral mass, wherein said integral mass is substantially pure 2 to 10 wt % carbonate-substituted hydroxyapatite that (i) has a calcium/phosphate molar ratio of about 1.33 to 2.0, (ii) is not sintered or hydrothermally prepared, (iii) has a compressive strength ranging from about 5620 to 11794 psi, and (iv) is biocompatible, said kit comprising:

dry ingredients comprising $Ca(H_2PO_4)_2.H_2O$, a tricalcium phosphate, and calcium carbonate in an amount ranging from about 9.33 to 40 wt % of said dry ingredients; and a 0.01 to 2M sodium phosphate solution at pH 6 to 11, wherein said sodium phosphate solution is physically separated from the dry ingredients of said kit and is present in an amount ranging from about 15 to 50 wt % of the total weight of said dry ingredients and said sodium phosphate solution of said kit.

14. A kit for use in the preparation of a composition capable of hardening and forming an integral mass, wherein said integral mass is substantially pure 2 to 10 wt % carbonate-substituted hydroxyapatite that (i) has a calcium/phosphate molar ratio of about 1.33 to 2.0, (ii) is not sintered or hydrothermally prepared, (iii) has a compressive strength ranging from about 5620 to 11794 psi, and (iv) is biocompatible, said kit comprising:

dry ingredients comprising $Ca(H_2PO_4)_2.H_2O$, a tricalcium phosphate, and calcium carbonate in an amount ranging from about 9.33 to 18 wt % of said dry ingredients; and a 0.01 to 2M sodium phosphate solution at pH 6 to 11, wherein said sodium phosphate solution is physically separated from the dry ingredients of said kit and is present in an amount ranging front about 15 to 50 wt % of the total weight of said dry ingredients and said sodium phosphate solution of said kit.

* * * * *